United States Patent [19]

Morris

[11] 4,127,582

[45] Nov. 28, 1978

[54] METHOD OF PREPARING ALKYL HALOPYRIDINYLOXYALKANOATES

[75] Inventor: Leo R. Morris, Midland, Mich.

[73] Assignee: The Dow Chemical Company, Midland, Mich.

[21] Appl. No.: 754,796

[22] Filed: Dec. 27, 1976

[51] Int. Cl.$^2$ .............................................. C07D 213/79
[52] U.S. Cl. ................................... 546/302; 546/301; 546/303
[58] Field of Search .................................... 260/295 R
[56] References Cited

U.S. PATENT DOCUMENTS

| | | | |
|---|---|---|---|
| 3,609,158 | 9/1971 | Torba | 260/295 R |
| 3,751,421 | 8/1973 | Nyquist et al. | 260/295 R |
| 3,761,486 | 9/1973 | McGregor | 260/295 R |

*Primary Examiner*—Alan L. Rotman
*Attorney, Agent, or Firm*—Daniel L. De Joseph; C. Kenneth Bjork

[57] ABSTRACT

A novel method for the preparation of alkyl halopyridinyloxyalkanoate compounds is disclosed, which comprises reacting a halopyridine with an alkyl alpha-hydroxy alkanoate in the presence of an alkali metal carbonate promoter.

The ester products prepared from this method are useful as herbicides.

18 Claims, No Drawings

METHOD OF PREPARING ALKYL HALOPYRIDINYLOXYALKANOATES

BACKGROUND OF THE INVENTION

It is well known that certain halo-2-pyridinyloxy compounds are useful as herbicides. Such compounds are prepared by a number of methods. For example, U.S. Pat. No. 3,814,774 teaches preparing a 3,5-dichloro-2-pyridinyloxyethyl hydrocarbon ether,

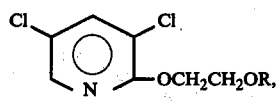

where R is an aliphatic or aromatic radical by using a two-step process:

(a) reacting the mono ether of ethylene glycol with an alkali metal hydride, such as sodium hydride in an inert solvent such as tetrahydrofuran to make the alkali metal salt of the mono ether of ethylene glycol, and (b) reacting this alkali metal salt with 2,3,5-trichloropyridine at about 50° C. in the presence of a trace amount of copper powder to form the desired dichloropyridinyloxyethyl ether.

U.S. Pat. No. 3,862,952 teaches preparing 3,5,6-trichloro-2-pyridinyloxyacetic acid,

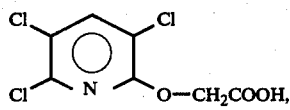

by reacting 2,3,5,6-tetrachloropyridine with paraformaldehyde and an alkali-metal cyanide in an anhydrous water-miscible inert aprotic solvent (such as dimethyl sulfoxide or acetonitrile) to form 3,5,6-trichloro-2-pyridinyloxyacetonitrile, which is then converted to the desired product by aqueous acid hydrolysis.

SUMMARY OF THE INVENTION

The present invention is a one-step method of preparing alkyl halopyridinyloxyalkanoates by reacting a halopyridine with an alkyl alpha-hydroxy alkanoate (hereinafter referred to also as an alkyl hydroxy alkanoate), in the presence of an alkali metal carbonate promoter, such as sodium carbonate. The resulting alkyl halopyridinyloxyalkanoates are useful as herbicides.

DETAILED DESCRIPTION OF THE INVENTION

In accordance with the novel method of the present invention, a halopyridine is reacted with an alkyl hydroxy alkanoate in the presence of an alkali metal carbonate promoter to form the corresponding alkyl halopyridinyloxyalkanoate.

Suitable pyridine starting materials for the present invention are halopyridines which correspond to the following formula:

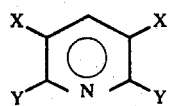

wherein each X and each Y substituent is individually selected from the group consisting of chlorine, fluorine, bromine and hydrogen; with the proviso that both Y substituents are not hydrogen. Examples of suitable starting pyridine compounds are 2,3,5,6-tetrachloropyridine, 2,3,5-trichloropyridine, 3,5-dichloro-2,6-difluoropyridine, 2,5-dichloropyridine, 2,6-dichloropyridine and 2,3,6-trichloropyridine.

Suitable lower alkyl hydroxy alkanoate starting materials for the present invention correspond to the following formula:

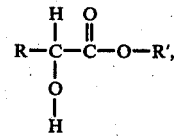

wherein R is either hydrogen or $CH_3$ and R' is either (a) a straight or branched chain alkyl group of from 1 to 4 carbon atoms or (b) a moiety of the formula $RCHCH_2OR_1$, wherein $R_1$ is a straight or branched chain alkyl group of from 1 to 4 carbon atoms and R is as defined hereinbefore.

Examples of suitable lower alkyl hydroxy alkanoate starting materials are ethyl lactate, methyl lactate, methyl glycolate, ethyl glycolate, n-propyl glycolate, isopropyl glycolate, and n-butyl glycolate, sec-butyl glycolate, isobutyl glycolate, and tert-butyl glycolate.

Sodium carbonate is the preferred alkali metal carbonate promoter. It is understood, however, that "alkali metal carbonate" as used throughout this specification and claims includes both carbonates and bicarbonates. Examples of other suitable alkali metal carbonate promoters are sodium bicarbonate, potassium carbonate, and potassium bicarbonate. It is preferred that the alkali metal carbonate be anhydrous.

The present invention's novel process will, therefore, proceed according to the unbalanced equation:

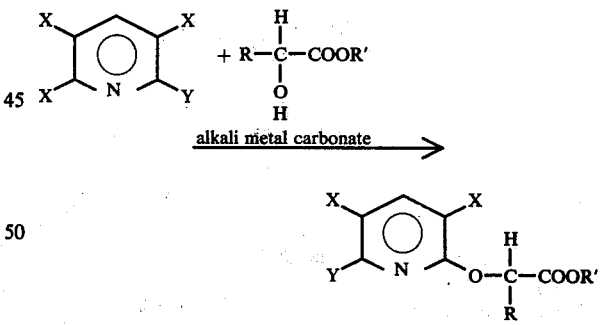

wherein X, Y, R and R' are as set forth hereinbefore.

In practicing the present invention, the halopyridine, alkyl alpha-hydroxy alkanoate, and the alkali metal carbonate promoter are mixed in a reaction vessel. It should be noted that the precise order of the addition of the above components to the reaction vessel is not critical to this invention.

At atmospheric pressure, the contents of the reaction vessel are agitated while at a temperature of from about 90° C. to about 150° C., and preferably from about 100° C. to about 140° C., for from about 1 to about 24 hours. The reaction will take place at temperatures below about 90° C.; however, at such temperatures the rate of reaction is slower and more impurities, such as haloalkanoxy pyridines, are formed. A practical upper temperature limit is the boiling point of the alkyl alpha-hydroxy alkanoate; for example, the b.p. of methyl glycolate is about 151.2° C. and the b.p. of ethyl glycolate is about 160° C. It is understood, however, that the reaction can be run at temperatures in excess of the b.p. of the alkyl alpha-hydroxy alkanoate if the reaction mixture is subjected to sufficient pressure.

In the practice of the present invention the mole ratio of the alkyl hydroxy alkanoate to the halopyridine should be in excess of 1 and, preferably, the lower limit of this mole ratio is about 3. Product formation is realized when the mole ratio is between 1 and about 3; however, within that ratio range more impurities, such as haloalkanoxy pyridines, are formed. The upper limit of the above mole ratio can be left to the discretion of the individual practitioner of this invention, although the rate of reaction and the yield of the desired product does not increase significantly when the mole ratio is in excess of about 10.

It is preferred that the mole ratio of the alkali metal carbonate to the halopyridine be at least 1. Product preparation proceeds when the ratio is below 1, but the rate of reaction is slower and the yield of the desired alkanoate product ordinarily is less than when the above ratio is 1 or more. There is no advantage, in terms of the rate of reaction or product yield, in having the above ratio greater than about 2, although it is understood that the individual practitioner of this invention may, depending upon his particular needs, run the instant reaction with a carbonate/halopyridine molar ratio in excess of 2.

Within the preferred temperature and mole ratio ranges for the process when run at atmospheric pressure, there is usually from about 5% to about 90% yield of the alkyl hydroxy alkanoate product after about 1 hour, depending upon the reactants utilized. If the process is allowed to proceed for a longer time the yield of the alkyl halopyridinyloxyalkanoate usually increases. However, any additional yield realized after about 24 hours may not, depending on the needs of the individual practitioner of this invention, be sufficient to economically justify continuing the preparation past that time.

Purification and isolation of the desired alkyl halopyridinyloxyalkanoate product can be made by any of a number of methods, such as by extraction, crystallization, or distillation, that are well known to those skilled in the art.

If the product is isolated by washing the solution with water, the ester will undergo hydrolysis if the solution is basic (from unreacted alkali metal carbonates). Therefore, the solution should be acidified prior to the washing step.

It has been discovered that, as a side reaction, there will be base catalyzed polymerization of the hydroxy alkanoate with the resulting loss of an alcohol as per the following equilibrium equation:

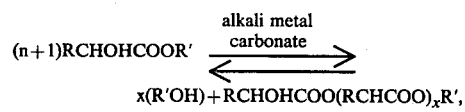

wherein R' and R are as set forth hereinbefore and $n$ is a positive integer.

The alcohol formed in the above ester polymerization will compete with the monomeric hydroxy alkanoate for reaction with the halopyridine as exemplified by the following illustration wherein the alcohol is methanol, the halopyridine is 2,3,5,6-tetrachloropyridine, and the alkali metal carbonate base is sodium carbonate:

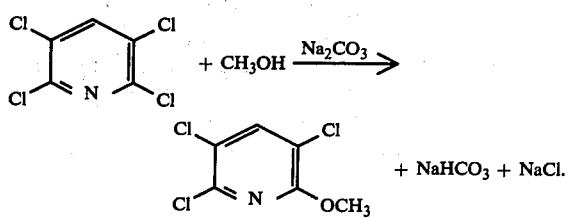

Thus, the reaction of the alcohol with the halopyridine will result in the formation of a haloalkanoxy pyridine, with a resulting decrease in the yield of the desired alkyl halopyridinyloxyalkanoate product. It is desirable, therefore, to periodically strip the alcohol from the reaction system.

It has also been discovered that, in another side reaction, oligimers of the alkyl halopyridinyloxyalkanoate will be formed from ester interchange reactions as well as from direct reactions of the polymeric hydroxy alkanoate with the halopyridine. An example of the latter reaction in which the halopyridine is 2,3,5-trichloropyridine, follows:

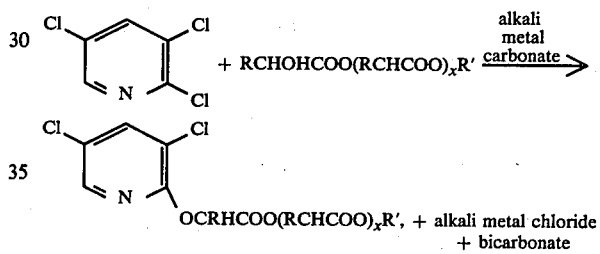

wherein R', R and $n$ are as set forth hereinbefore.

It has been discovered that these oligomeric alkyl halopyridinyloxyalkanoate side products and the polymers of the hydroxy alkanoate can be converted to their desired monomeric state by adding the stripped alcohol and additional fresh alcohol to the base-catalyzed reaction system. The alcohol, because of its above-discussed tendency to react with the halopyridine, should be, therefore, added to the reaction system at a time when the reaction is substantially complete, i.e., when most of halopyridine has reacted to form the desired product or the oligimer thereof.

The examples which follow further illustrate the present invention and the manner in which it can be practiced; these examples should be construed merely as being representative and not as a limitation on the overall scope of the invention.

EXAMPLE 1

A reaction vessel was charged with 43.4 g (0.2 mole) of 2,3,5,6-tetrachloropyridine, 108 g (1.2 mole) of methyl glycolate, and 26.6 g (0.25 mole) of anhydrous sodium carbonate. The resulting mixture was stirred and heated to 110° C. at atmospheric pressure with methanol distillate being removed, as it formed, through a distillation head. After 3.5 hours, 6.5 g of methanol distillate was collected. This distillate, along with 64.0 g of additional methanol was added to the reaction mixture and reflux was continued for 1 hour.

The solution was cooled to room temperature and anhydrous hydrogen chloride was sparged in slowly, until the solution was acidic to thereby minimize hydrolysis. The solution was refluxed at 70° C. for two more hours, and volatiles were removed in a vacuum. One hundred and eighteen grams of methanol and methyl glycolate were recovered. Perchloroethylene (150 g) was used to extract the ester. After washing the resulting perchloroethylene solution with water and cooling to 20° C., crystals of the product precipitated. These crystals were filtered and dried to give 41.2 g (0.15 mole) of methyl 3,5,6-trichloro-2-pyridinyloxyacetate, m.p. 99°–103° C. The ester product was analyzed by gas-liquid chromatography and was shown to be about 98% pure. Further recrystallization from methanol gave the pure ester, m.p. 104.5°–106° C. In the filtrate from the original crystallization there was another 8.2 g (0.03 mole) of product, and therefore, the total amount of product was 49.4 g (0.18 mole), which represented a 90% yield based on the tetrachloropyridine.

EXAMPLE 2

A reaction vessel was charged with 108 g (1.2 mole) of methyl glycolate and 19.9 (0.188 mole) of anhydrous sodium carbonate. The reaction vessel was heated to 110° C. with the methanol distillate being periodically removed. Thirty two and six tenths grams (32.6 g, 0.15 mole) of 2,3,5,6-tetrachloropyridine was added into the reaction vessel in three substantially equal portions over 15 minutes, with the reaction temperature remaining at 110° C. Methanol was continually stripped as it condensed, giving a total methanol distillate of about 7 g. This distillate, along with 96 g of fresh methanol, was added to the reaction mixture and the alcohol was thereafter refluxed at 70° C. After 1.5 hours of reflux, anhydrous HCl was sparged in until a pH of 1.0 was obtained. The mixture was then refluxed for 1.5 hours. After filtration of the salt and washing with methanol, it was determined by gas-liquid chromatography that there was 35.4 g (0.131 mole) of the methyl 3,5,6-trichloro-2-pyridinyloxyacetate in the filtrate. The total yield of the desired product from the tetrachloropyridine was 87%.

EXAMPLE 3

In this example the ester product, ethyl 2-(3,5,6-trichloro-2-pyridinyloxy)propionate, was converted to its corresponding carboxylic acid, 2-(3,5,6-trichloro-2-pyridinyloxy)propionic acid in situ and prior to recovery.

A reaction vessel was charged with 23.7 g (0.2 mole) of ethyl lactate, 6.5 g (0.03 mole) of 2,3,5,6-tetrachloropyridine, and 4.0 g (0.038 mole) of anhydrous sodium carbonate. The mixture was heated to 140°–150° C. for 11 hours, with the volatiles being allowed to distill. Glc analysis indicated 65% conversion of the tetrachloropyridine to products. The ester product was then isolated as its corresponding free acid by extracting the aromatics from the reaction mixture (which was diluted by water) with methylene chloride, concentration to remove th solvent, and refluxing for one hour with excess 5% sodium hydroxide. The aqueous phase was cooled, extracted with methylene chloride and acidified with dilute hydrochloric acid. The precipitate was then filtered. Two recrystallizations of the solid from a methanol-water mixture gave a white powder, m.p. 182.5°–184.2° C., which nmr analysis confirmed as 2-(3,5,6-trichloro-2-pyridinyloxy)propionic acid.

EXAMPLE 4

A reaction vessel was charged with 45.0 g (0.5 mole) of methyl glycolate and 13.3 g (0.125 mole) of anhydrous sodium carbonate. The resulting mixture was heated to 110° C. for 10 minutes, with methanol being allowed to strip off as it condensed. Thereafter 18.4 g (0.1 mole) of 3,5-dichloro-2,6-difluoropyridine was added to the reaction vessel, and the mixture was stirred at 110° C. for 1 hour. The stripped methanol (approximately 4 ml) and 64 g of fresh methanol were added to the slurry, which was refluxed for 1 hour at 70° C. and filtered. The filtrate was cooled to approximately 10° C. to give fine white crystals which were filtered, washed with cold methanol, and air dried. The resulting solid was further purified by being dissolved in warm perchloroethylene, filtered and cooled to give a solid precipitate. Filtration and air-drying gave 12.0 of a solid product which was identified by gas-liquid chromatography and nuclear magnetic resonance to be the desired product, 3,5-dichloro-6-fluoro-2-pyridinyloxyacetate, m.p. 72.2°–73.0° C., of approximately 99% purity. The filtrates from the previous isolations were combined and concentrated by vacuum stripping. The residue was extracted twice with hot methylene chloride, and the filtered extracts were concentrated to remove the solvent, leaving 11.0 g of product which solidified on cooling. Analysis by gas-liquid chromatography and nuclear magnetic resonance indicated that the product contained 9.3 g of methyl-3,5-dichloro-6-fluoro-2-pyridinyloxyacetate and 1.7 g of various impurities. Therefore, approximately 21.3 g (0.083 mole) of the desired product was isolated, which represents an 83% yield based on the halopyridine.

What is claimed is:

1. A method for preparing alkyl halopyridinyloxyalkanoate compounds which comprises: reacting
   (a) a halopyridine of the formula

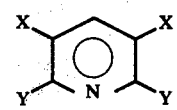

wherein each X and each Y substituent is individually selected from the group consisting of chlorine, fluorine, bromine and hydrogen, with the proviso that both Y substituents are not hydrogen, and
   (b) an alkyl hydroxy alkanoate of the formula

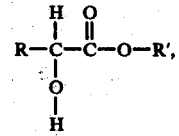

wherein R is either hydrogen or $CH_3$ and R' is either (i) a straight or branched chain alkyl group of from 1 to 4 carbon atoms or (ii) a moiety of the formula $RCHCH_2OR_1$, wherein $R_1$ is a straight or branched chain alkyl group of from 1 to 4 carbon atoms;
in the presence of an alkali metal carbonate promoter thereby to produce an alkyl halopyridinyloxyalkanoate compound.

2. The method of claim 1 wherein the alkali metal carbonate promoter is sodium carbonate.

3. The method of claim 1 wherein the reaction is at atmospheric pressure and the reaction temperature ranges from about 90° C. to about 150° C.

4. The method of claim 1 wherein the mole ratio of the alkyl hydroxy alkanoate to the halopyridine is at least about 3.

5. The method of claim 1 wherein the mole ratio of the alkali metal carbonate to the halopyridine is at least 1.

6. The method lof claim 1 wherein the halopyridine is 2,3,5,6-tetrachloropyridine.

7. The method of claim 1 wherein the halopyridine is 2,3,5-trichloropyridine.

8. The method of claim 1 wherein the halopyridine is 3,5-dichloro-2,6-difluoropyridine.

9. The method of claim 1 wherein the alkyl hydroxy alkanoate is methyl glycolate.

10. The method of claim 1 wherein the alkyl hydroxy is ethyl lactate.

11. The method of claim 1 wherein the halopyridine is 2,3,5,6-tetrachloropyridine, the alkyl hydroxy alkanoate is methyl glycolate, the alkali metal carbonate promoter is sodium carbonate, the reaction is at atmospheric pressure and the reaction temperature ranges from about 90° C. to about 150° C.

12. The method of claim 11 wherein the mole ratio of methyl glycolate to 2,3,5,6-tetrachloropyridine is at least about 3 and the mole ratio of sodium carbonate to 2,3,5,6-tetrachloropyridine is at least 1.

13. The method of claim 1 wherein the halopyridine is 2,3,5-trichloropyridine, the alkyl hydroxy alkanoate is methyl glycolate, the alkali metal carbonate promoter is sodium carbonate, the reaction is at atmospheric pressure and the reaction temperature ranges from about 90° C. to about 150° C.

14. The method of claim 13 wherein the mole ratio of methyl glycolate to 2,3,5-trichloropyridine is at least about 3 and the mole ratio of sodium carbonate to 2,3,5-trichloropyridine is at least 1.

15. The method of claim 1 wherein the halopyridine is 3,5-dichloro-2,6-difluoropyridine, the alkyl hydroxy alkanoate is methyl glycolate, the alkali metal carbonate promoter is sodium carbonate, the reaction is at atmospheric pressure and the reaction temperature ranges from about 90° C. to about 150° C.

16. The method of claim 15 wherein the mole ratio of methyl glycolate to 3,5-dichloro-2,6-difluoropyridine is at least about 3 and the mole ratio of sodium carbonate to 3,5-dichloro-2,6-difluoropyridine is at least 1.

17. The method of claim 1 wherein the halopyridine is 2,3,5,6-tetrachloropyridine, the alkyl hydroxyalkanoate is ethyl lactate, the alkali metal carbonate promoter is sodium carbonate, the reaction is at atmospheric pressure and the reaction temperature ranges from about 90° C. to about 150° C.

18. The method of claim 17 wherein the mole ratio of ethyl lactate to 2,3,5,6-tetrachloropyridine is at least about 3 and the mole ratio of sodium carbonate to 2,3,5,6-tetrachloropyridine is at least 1.

* * * * *

UNITED STATES PATENT AND TRADEMARK OFFICE
CERTIFICATE OF CORRECTION

PATENT NO. : 4,127,582
DATED : November 28, 1978
INVENTOR(S) : Leo R. Morris

It is certified that error appears in the above-identified patent and that said Letters Patent are hereby corrected as shown below:

In column 2, line 2, delete "1of" and insert -- of --.

In column 2, line 45, delete " 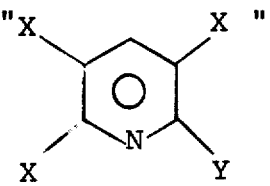 "

and insert -- 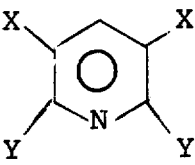 --.

In column 5, line 6, after grams insert -- (118 g.) --.

In column 5, line 61, delete "th" and insert -- the --.

In column 7, line 11, delete "1of" and insert -- of --.

Signed and Sealed this

First Day of May 1979

[SEAL]

Attest:

RUTH C. MASON
Attesting Officer

DONALD W. BANNER
Commissioner of Patents and Trademarks